United States Patent
Kim et al.

(10) Patent No.: US 11,045,308 B2
(45) Date of Patent: Jun. 29, 2021

(54) ARTIFICIAL CORNEA AND METHOD FOR MANUFACTURING THE ARTIFICIAL CORNEA

(71) Applicants: LEMON Co., Ltd, Gyeongsangbuk-do (KR); SHINSHU UNIVERSITY, Nagano (JP)

(72) Inventors: Ik Soo Kim, Nagano (JP); Davood Kharaghani, Nagano (JP); Ohtani Hijiri, Nagano (JP)

(73) Assignees: LEMON Co., Ltd, Gyeongsangbuk-do (KR); SHINSHU UNIVERSITY, Gyeongsangbuk-do (KR)

( * ) Notice: Subject to any disclaimer, the term of this patent is extended or adjusted under 35 U.S.C. 154(b) by 93 days.

(21) Appl. No.: 16/016,609

(22) Filed: Jun. 24, 2018

(65) Prior Publication Data
US 2019/0298511 A1    Oct. 3, 2019

(30) Foreign Application Priority Data
Mar. 28, 2018    (JP) .............................. JP2018-061526

(51) Int. Cl.
*A61F 2/14*    (2006.01)
*D04H 1/728*    (2012.01)
(Continued)

(52) U.S. Cl.
CPC ................ *A61F 2/142* (2013.01); *A61F 2/15* (2015.04); *D01F 1/10* (2013.01); *D01F 6/14* (2013.01); *D04H 1/4309* (2013.01); *D04H 1/728* (2013.01); *D06M 11/71* (2013.01); *D06M 15/333* (2013.01); *A61F 2230/0006* (2013.01);
(Continued)

(58) Field of Classification Search
CPC .... A61F 2/142; A61F 2/15; A61F 2/14; A61L 27/20; C08L 1/284
See application file for complete search history.

(56) References Cited

U.S. PATENT DOCUMENTS

2014/0330374 A1*  11/2014  Murphy .................. A61F 9/007
                                                     623/5.12

FOREIGN PATENT DOCUMENTS

CN    201810684914.2  A    6/2018
JP    2000-325369  A    11/2000
(Continued)

OTHER PUBLICATIONS

Bakhshandeh et al., Poly (epsilon-caprolactone) nanofibrous ring surrouding a polyvinyl alcohol hydrogel for the development pf a biocompatible two-prt artifical cornea, 2011, International Journal of Nanomedicine, vol. 6, pp. 1509-1515 (Year: 2011).*
(Continued)

*Primary Examiner* — Dah-Wei D. Yuan
*Assistant Examiner* — Andrew J Bowman
(74) *Attorney, Agent, or Firm* — Patshegen IP LLC; Moshe Pinchas

(57) ABSTRACT

Provided are an artificial cornea having sufficient strength and optical properties, in which deviation or infection of the artificial cornea is restrained, and a method for manufacturing the artificial cornea. According to the present invention, the method for manufacturing the artificial cornea includes a nonwoven fabric preparation step of preparing a nonwoven fabric formed therein with a through-hole, and a gel arrangement step of arranging an aqueous polymer gel to cover the through-hole.

6 Claims, 13 Drawing Sheets

(51) Int. Cl.
    *D04H 1/4309*    (2012.01)
    *D01F 1/10*      (2006.01)
    *D06M 11/71*     (2006.01)
    *D01F 6/14*      (2006.01)
    *D06M 15/333*    (2006.01)
    *D06M 101/24*    (2006.01)

(52) U.S. Cl.
    CPC ... *A61F 2240/001* (2013.01); *D06M 2101/24* (2013.01); *D10B 2321/06* (2013.01); *D10B 2509/00* (2013.01)

(56) References Cited

FOREIGN PATENT DOCUMENTS

| | | |
|---|---|---|
| JP | 5051424 B2 | 10/2012 |
| JP | 2018-061526 A5 | 7/2019 |
| KR | 10-2018-0055210 A | 5/2018 |
| WO | 2016-199139 A1 | 12/2016 |

OTHER PUBLICATIONS

Office Action in the Korean counterpart application KR 10-2018-0055210; dated Dec. 17, 2019.

* cited by examiner

ARTIFICIAL CORNEA AND METHOD FOR MANUFACTURING THE ARTIFICIAL CORNEA

BACKGROUND OF THE INVENTION

1. Field of the Invention

The present invention relates to an artificial cornea and a method for manufacturing an artificial cornea.

2. Description of the Related Art

A cornea is one of tissues constituting an eye (eyeball), and is a transparent film having a thickness of about 0.5 mm to 0.7 mm. A problem such as blurred vision that occurs in the cornea is called a corneal disease, and the corneal disease is a third leading cause of blindness in the world. At present, it is estimated that more than 10 million people in the world are being blinded by the corneal disease.

Corneal transplantation is generally known as a treatment for the corneal disease. However, since biological tissues of other people are transplanted into a patient in the corneal transplantation, rejection or infection may occur. In addition, the number of corneal suppliers is insufficient.

In this current environment, the use of artificial corneas instead of corneas taken from living bodies is under consideration.

In early artificial corneas, almost entire part of the artificial cornea is often formed of a dense transparent inorganic material (such as glass) and a transparent resin (such as polymethacrylate) (for example, see Patent Document 1). However, such an artificial cornea has low adhesiveness to biological tissues and applies mechanical stress to an eyeball, deviation or infection of the artificial cornea may easily occur, and it is very difficult to use the artificial cornea for a long period of time.

Recently, based on the above problems, an artificial cornea formed of a soft material or a fibrous material (for example, nonwoven fabric) having high biocompatibility, such as collagen, has been researched (for example, see Patent Document 2). Since such an artificial cornea may enable oxygen and nutrients, which are intimate with cells, to pass therethrough after transplantation, the above-described problems (such as deviation or infection of the artificial cornea) can be restrained.

(Patent document 1) JP Application Publication No. 63-99860 B (Patent document 2) JP 2008-43419 B

SUMMARY OF THE INVENTION

However, it is difficult for the artificial cornea formed of a soft material to have sufficient strength. In addition, there is a problem in the above patent documents that it is difficult for the artificial cornea formed of a fibrous material to obtain sufficient optical properties (such as high transparency, an appropriate refractive index, or low scattering properties).

To solve the problems described above, an object of the present invention is to provide an artificial cornea capable of restraining the problems of the conventional artificial corneas (such as deviation or infection) and having sufficient strength and excellent optical properties, and a method for manufacturing the artificial cornea.

According to the present invention, an artificial cornea includes: a nonwoven fabric formed therein with a through-hole; and an aqueous polymer gel arranged to cover the through-hole.

According to the present invention, a method for manufacturing an artificial cornea includes: a nonwoven fabric preparation step of preparing a nonwoven fabric formed therein with a through-hole; and a gel arrangement step of arranging an aqueous polymer gel to cover the through-hole.

In addition, fibers forming the nonwoven fabric may include nanofibers.

In addition, the fibers forming the nonwoven fabric may include polyvinyl alcohol-based nanofibers.

In addition, the nonwoven fabric may include a composite nanofiber of polyvinyl alcohol, hydroxyethyl cellulose, and graphite (PVA-HEC-GR).

In addition, the nonwoven fabric may be formed through an electrospinning scheme using a spinning solution as a source material obtained by dispersing the graphite in a mixed solution of the polyvinyl alcohol and the hydroxyethyl cellulose.

In addition, a hydroxyapatite (HA) may be attached to the nonwoven fabric.

In addition, the nonwoven fabric preparation step may include attaching the hydroxyapatite to the nonwoven fabric by performing one time or several times of a cycle of immersing the nonwoven fabric in an aqueous solution of calcium chloride, and immersing the nonwoven fabric in an aqueous solution of disodium phosphate (DSP) ($Na_2HPO_4$) adjusted to pH 10 or more.

In addition, the aqueous polymer gel may include a polyvinyl alcohol-based aqueous polymer gel.

In addition, the gel arrangement step may include arranging the aqueous polymer gel on the nonwoven fabric by a freeze-thawing scheme.

According to the present invention, the artificial cornea is formed of a nonwoven fabric, which is intimate with human cells, so that efficient transmission of oxygen and nutrients as well as the strength of the artificial cornea can be ensured without causing rejection.

In addition, according to the artificial cornea of the present invention, the through-hole is formed in the nonwoven fabric, and the aqueous polymer gel is arranged to cover the through-hole, so that light passing through the artificial cornea may not be affected by the nonwoven fabric. Therefore, according to the present invention, the artificial cornea can obtain sufficient strength and optical properties while restraining the conventional problems.

According to the present invention, the method for manufacturing the artificial cornea includes a nonwoven fabric preparation step of preparing a nonwoven fabric formed therein with a through-hole, and a gel arrangement step of arranging an aqueous polymer gel to cover the through-hole, so that an artificial cornea having sufficient strength and optical properties can be manufactured while restraining the problems of the conventional artificial cornea.

DETAILED DESCRIPTION OF THE INVENTION

Hereinafter, an artificial cornea and a method for manufacturing an artificial cornea according to the present invention will be described with reference to embodiments. However, configurations described in the embodiments and combinations thereof are not essential to the technical solution of the present invention.

1. Artificial Cornea 1 According to an Embodiment

Figure 1:
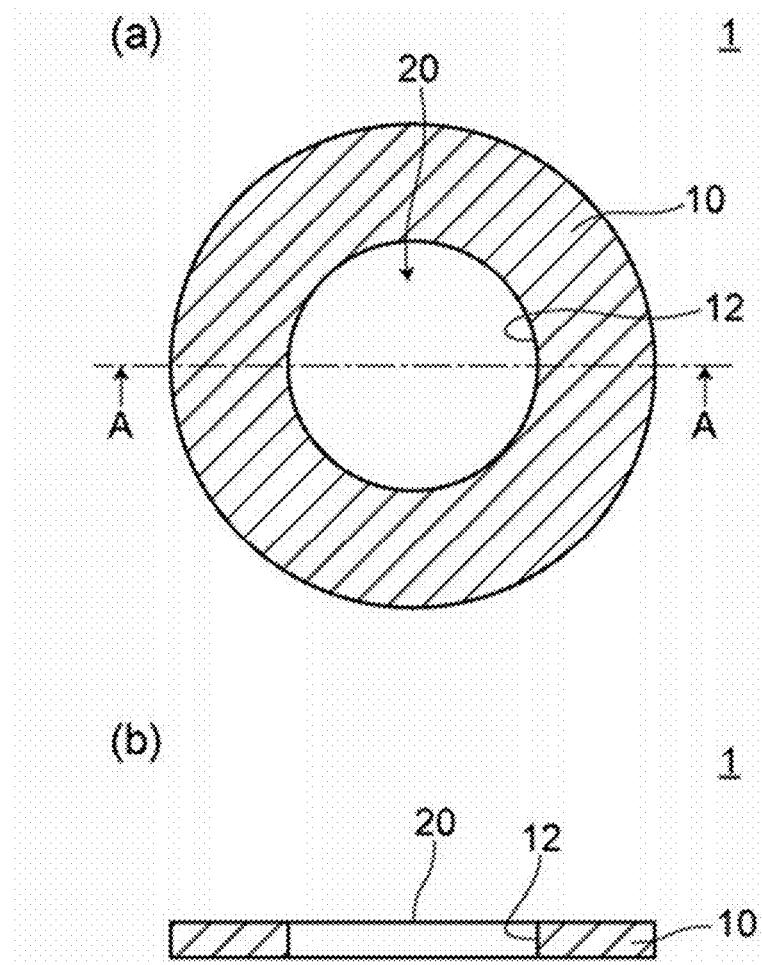
FIG. 1 is a view for explaining an artificial cornea according to an embodiment.

FIG. 1 is a view for explaining an artificial cornea 1 according to an embodiment. FIG. 1A is a plan view showing the artificial cornea 1, and FIG. 1B is a sectional view taken along line A-A of FIG. 1A.

First, the artificial cornea 1 according to the embodiment will be described.

In the artificial cornea 1 according to the embodiment, as shown in FIG. 1, a nonwoven fabric 10 formed therein with a through-hole 12 includes an aqueous polymer gel 20 arranged to cover the through-hole 12.

A size of the artificial cornea 1 may be appropriately set according to the purpose of use (transplantation target). In general, a thickness of the artificial cornea may be about 0.5 mm to 0.7 mm for an adult.

The nonwoven fabric 10 has a circular external shape when view from a top, and the through-hole 12 is formed at a center of the circle. The nonwoven fabric 10 may be referred to as a base substrate for the aqueous polymer gel 20.

Fibers constituting the nonwoven fabric 10 may be formed of any materials having various diameters as long as they do not degrade the effects of the present invention. However, the fibers constituting the nonwoven fabric 10 are preferably nanofibers.

The nanofiber is a fiber having a nanoscale fiber diameter (for example, a fiber diameter of 3000 nm or less, preferably an average fiber diameter of 1000 nm or less). The nanofiber has properties (for example, a very large specific surface area) different from those of ordinary fibers having a microscale fiber diameter or greater, and is utilized in various fields. In the embodiment, the fiber diameter of the nanofiber preferably ranges from 50 nm to 500 nm.

More preferably, the fibers constituting the nonwoven fabric 10 are polyvinyl alcohol (PVA)-based nanofibers. The PVA-based nanofiber refers to a nanofiber containing a component having polyvinyl alcohol as a source material, as a main component (component of 30% or more by weight).

In addition, since the PVA is a water-soluble polymer, when a PVA-based polymer is used as a source material for the nonwoven fabric, it is basically necessary to perform an insolubilization treatment (for example, a cross-linking treatment using glutaraldehyde (GA), heat, ultraviolet (UV), etc.). The necessity and a specific scheme of the insolubilization treatment for PVA are generally known, so that detailed description of the insolubilization treatment will be omitted in the following description.

In the embodiment, the nonwoven fabric 10 includes a polyvinyl alcohol-hydroxyethyl cellulose-graphite (PVA-HEC-GR) composite nanofiber.

The PVA-HEC-GR composite nanofiber is obtained by dispersing graphite (GR) between nanofibers formed of a source material in which polyvinyl alcohol (PVA) and hydroxyethyl cellulose (HEC) are mixed. In addition, it is unnecessary for the graphite to be nanosized, and the graphite may be used, for example, when a length of a longest portion of the graphite is 20 μm or less.

In addition to the above-described configuration, according to the present invention, a nonwoven fabric formed of nanofibers, which are formed by using a material having high biocompatibility as a source material such as chitosan, gelatin-PVA, cellulose, or poly-L-lactic acid, can be used.

In the embodiment, hydroxyapatite (HA) is attached to the nonwoven fabric 10. The hydroxyapatite may be physically or chemically attached to the nonwoven fabric 10.

The aqueous polymer gel 20 is arranged to cover the through-hole 12. The aqueous polymer gel 20 may be expressed as "arranged to fill the through-hole 12", and may be expressed as "arranged inside the through-hole".

The aqueous polymer gel 20 includes a PVA-based water-soluble polymer gel. The aqueous polymer gel refers to a gel (hydrogel) having water in a three-dimensional net structure formed by a polymer. The PVA-based water-soluble polymer gel refers to an aqueous polymer gel containing a component having polyvinyl alcohol as a source material, as a main component. The PVA-based water-soluble polymer gel may be a polyvinyl alcohol hydrogel (PVA hydrogel) in which entire polymer is formed of a completely hydrolyzed polyvinyl alcohol. In addition, according to the present invention, polyhydroxyethyl methacrylate, polyvinyl pyrrolidone, silicone hydrogel, or the like may be used as the aqueous polymer gel.

2. Method for Manufacturing an Artificial Cornea According to an Embodiment

Figure 2:
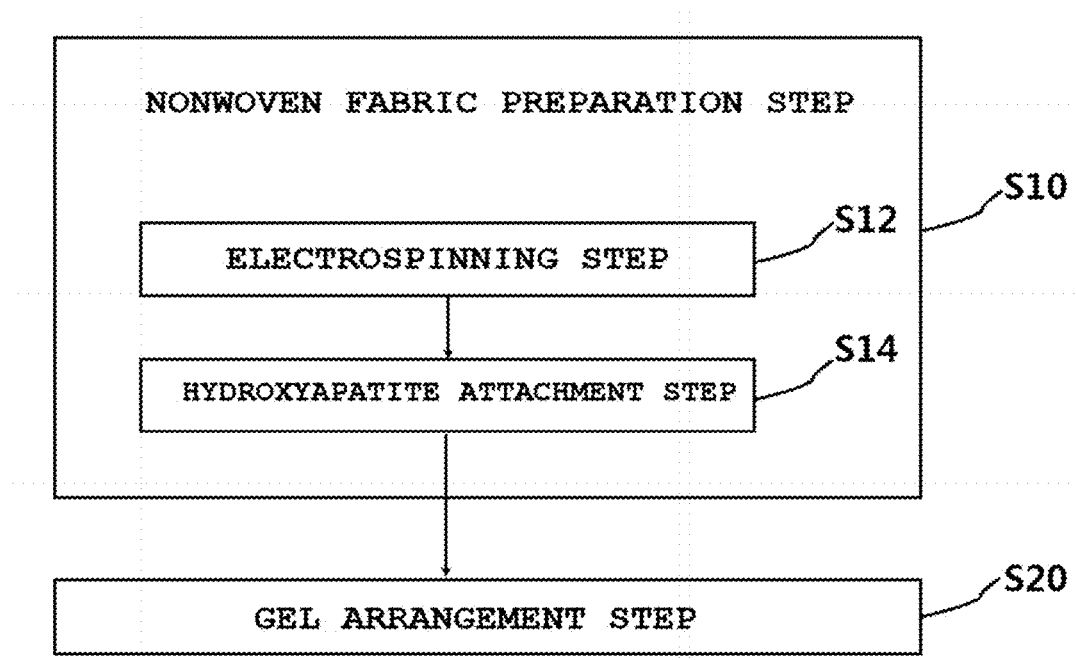
FIG. 2 is a flowchart of a method for manufacturing an artificial cornea according to an embodiment.

FIG. 2 is a flowchart of a method for manufacturing an artificial cornea according to an embodiment.

Next, a method for manufacturing an artificial cornea according to an embodiment will be described.

According to the embodiment, the method for manufacturing the artificial cornea includes a nonwoven fabric preparation step S10 and a gel arrangement step S20 as shown in FIG. 2.

The nonwoven fabric preparation step S10 is a step of preparing the nonwoven fabric 10 formed therein with the through-hole 12. The nonwoven fabric preparation step S10 includes an electrospinning step S12 and a hydroxyapatite attachment step S14.

The nonwoven fabric 10 to be prepared in the nonwoven fabric preparation step S10 is preferably a nonwoven fabric formed of nanofibers, more preferably PVA-based nanofibers.

In the embodiment, the nonwoven fabric 10 includes a composite nanofiber of polyvinyl alcohol-hydroxyethyl cellulose-graphite (PVA-HEC-GR). The nonwoven fabric 10 can be prepared by the electrospinning step S12.

The electrospinning step S12 is a step of obtaining the nonwoven fabric 10 formed of nanofibers by forming the nanofibers through an electrospinning (field emission) scheme.

In the electrospinning step S12, the nonwoven fabric 10 (composite nanofiber) is formed through the electrospinning scheme using a spinning solution as a source material obtained by dispersing the graphite in a mixed solution of polyvinyl alcohol and hydroxyethyl cellulose. Manufacture conditions of the nonwoven fabric (composite nanofiber) formed by the electrospinning will be described in the following examples, but the manufacture conditions are not limited thereto and can be changed within an appropriate range.

The nonwoven fabric 10 prepared in the nonwoven fabric preparation step S10 is attached with hydroxyapatite. The nonwoven fabric 10 may be prepared by the hydroxyapatite attachment step S14.

The hydroxyapatite attachment step S14 is a step of attaching the hydroxyapatite to the nonwoven fabric 10 by performing one time or several times of a cycle of immersing the nonwoven fabric 10 in an aqueous solution of calcium chloride ($CaCl_2$), and immersing the nonwoven fabric 10 in an aqueous solution of disodium phosphate (DSP) ($Na_2HPO_4$) adjusted to pH 10 or more.

In the above scheme, nanoscale hydroxyapatite is synthesized so as to be attached to the nonwoven fabric 10. In this case, hydroxy groups of the fibers constituting the nonwoven fabric 10 chemically bond with calcium ions, so that adhesiveness of the hydroxyapatite can be enhanced.

The step of attaching the hydroxyapatite to the nonwoven fabric is not limited to the above embodiment, and the hydroxyapatite may be attached to the nonwoven fabric by other processes (schemes).

Although the through-hole 12 is formed in the nonwoven fabric 10 prepared in the nonwoven fabric preparation step S10, the through-hole 12 can be formed at any step before the gel arrangement step S20. The through-hole 12 may be formed by, for example, cutting and punching. Meanwhile, the nonwoven fabric 10 may be initially formed with the through-hole 12. An outer peripheral shape of the nonwoven fabric 10 may be formed in the same manner.

The gel arrangement step S20 is a step of arranging the aqueous polymer gel 20 to cover the through-hole 12.

The aqueous polymer gel 20 includes a PVA-based water-soluble polymer gel. A PVA hydrogel may be used as the PVA-based water-soluble polymer gel.

In the gel arrangement step S20, the aqueous polymer gel 20 is arranged (fixed) on the nonwoven fabric 10 by a freeze-thawing scheme. Since the freeze-thawing scheme is a generally known technique, detailed description thereof will be omitted. In addition, the step of arranging the aqueous polymer gel 20 on the nonwoven fabric 10 is not limited to the above embodiment, and the aqueous polymer gel 20 may be arranged (fixed) on the nonwoven fabric 10 by other processes (schemes).

3. Effects of the Artificial Cornea 1 and the Method for Manufacturing the Artificial Cornea According to the Embodiment Hereinafter, effects of the artificial cornea 1 and the method for manufacturing the artificial cornea according to the embodiment will be described.

According to the embodiment, the artificial cornea 1 is formed of the nonwoven fabric 10, which is intimate with cells, so that efficient transmission of oxygen and nutrients as well as the strength of the artificial cornea can be ensured without causing rejection in a human body.

In addition, according to the artificial cornea 1 of the embodiment, the through-hole is formed in the nonwoven fabric 10, and the aqueous polymer gel 20 is arranged to cover the through-hole 12, so that light passing through the artificial cornea 1 may not be affected by the nonwoven fabric 10, thereby minimizing interference of the light.

According to the embodiment, the method for manufacturing the artificial cornea includes the nonwoven fabric preparation step S10 for preparing the nonwoven fabric 10 formed therein with the through-hole 12 and the gel arrangement step S20 of arranging the aqueous polymer gel 20 to cover the through-hole 12, so that the artificial cornea manufactured by the manufacturing method can achieve the above-described effects.

In addition, according to the method for manufacturing the artificial cornea of the embodiment, the fibers constituting the nonwoven fabric 10 are nanofibers, so that the strength and the specific surface area of the nonwoven fabric 10 can be sufficiently increased, and the manufactured artificial cornea 1 can be stably settled to a wound site.

Further, according to the method for manufacturing the artificial cornea of the embodiment, the fibers constituting the nonwoven fabric 10 are the PVA-based nanofibers so that high biocompatibility can be obtained, and the polyvinyl alcohol, which is a material suitable for nanofiber formation, may be used as a main material so that the nonwoven fabric 10 of the artificial cornea 1 can be stably settled to a wound site.

Moreover, according to the method for manufacturing the artificial cornea of the embodiment, since the nonwoven fabric 10 includes the composite nanofiber of polyvinyl alcohol-hydroxyethyl cellulose-graphite, hydroxyethyl cellulose is added to the artificial cornea, so that tensile strength of the nanofiber is increased. In addition, activity of biological tissues (cells) settled to the artificial cornea can be increased by the graphite (promoting vascularization, etc.).

In addition, according to the method for manufacturing the artificial cornea of the embodiment, the nonwoven fabric 10 is formed through an electrospinning scheme using a spinning solution as a source material obtained by dispersing the graphite in a mixed solution of the polyvinyl alcohol and the hydroxyethyl cellulose, so that the nonwoven fabric 10 may have less irregularity in fiber diameter and less aggregation of graphite.

Further, according to the method for manufacturing the artificial cornea of the embodiment, since the hydroxyapatite is attached to the nonwoven fabric 10, the activity of the biological tissues (cells) settled on the nonwoven fabric 10 can be increased, and integration of the artificial cornea and the eyeball can be promoted.

Moreover, according to the method for manufacturing the artificial cornea of the embodiment, in the nonwoven fabric preparation step S10, the hydroxyapatite is attached to the nonwoven fabric 10 by performing one time or several times of a cycle of immersing the nonwoven fabric 10 in the aqueous solution of calcium chloride, and immersing the nonwoven fabric 10 in the aqueous solution of disodium phosphate adjusted to pH 10 or more, so that the adhesiveness between the nonwoven fabric 10 and the hydroxyapatite can be enhanced, and an amount of hydroxyapatite can be easily controlled by changing the number of cycles.

In addition, according to the method for manufacturing the artificial cornea of the embodiment, the aqueous polymer gel 20 includes a PVA-based water-soluble polymer gel, so that the artificial cornea 1 can obtain better optical properties by using the PVA-based water-soluble polymer gel having excellent optical properties.

Further, according to the method for manufacturing the artificial cornea of the embodiment, in the gel arrangement step S20, the aqueous polymer gel 20 is arranged on the nonwoven fabric 10 by a freeze-thawing scheme, so that the nonwoven fabric 10 and the aqueous polymer gel 20 can be easily fixed to each other.

EXAMPLES

The artificial cornea was prepared according to the method for manufacturing the artificial corneal of the present invention, and results were observed and tested.

1. Reagents, Equipment, Etc. Used in Examples

First, reagents and equipment used in examples will be described.

In the method for manufacturing the artificial cornea according to the examples, analytical-grade reagents were used. Sodium hydroxide (NaOH purity: 97.0%), acetone, ethanol (99.5), 10 times of phosphate-buffered saline (PBS buffer; pH 7.4) and concentrated hydrochloric acid (HCl; 35.0% to 37.0%) purchased from Wako Pure Chemical Industries, Ltd were used. Dimethyl sulfoxide (DMSO), graphite powder (GR; <20 μm), polyvinyl alcohol (PVA, Mw: 85,000 to 124,000, degree of hydrolysis: 87% to 89%, and completely gelated) 2-hydroxymethyl cellulose (HEC, average Mw: 90,000), and disodium phosphate ($Na_2HPO_4$) purchased from Sigma-Aldrich, Inc. were used. Glutaraldehyde (GA; 50% aqueous solution) and calcium chloride ($CaCl_2$) purchased from MP Biomedicals, U.S.A. were used.

In a cytotoxicity test for the artificial cornea, analytical-grade reagents and the like were used. Dulbecco's Modified Eagle's Medium (DMEM)/Ham's F-12 medium, which is an animal cell culture medium, purchased from Sigma-Aldrich was used. Newborn calf serum (NBCS), a mixed solution of insulin-transferrin-selenium (Se) (ITS), and an epidermal growth factor (EGF; somatic cell recombination) from Gibco brand of Thermo Fisher Scientific were used. Calcium chloride ($CaCl_2$) purchased from Ajax Finechem was used.

24-well cell culture plates from Greiner Bio-One International were used.

Human corneal epithelium (HCE) cells were transferred from Dr. Ilene Gipson in Schepens Eye Research Institute.

Har-100*12 of Matsusada Precision, Inc. was used as a power supply device for the field emission.

An ATR-FTIR spectrum was measured using DuraSampIIR II manufactured by Smiths Detection, U.K. The measurement was performed at room temperature.

Rotaflex RTP300 manufactured by Rigaku coporation, Inc. was used for measuring X-ray diffraction patterns (XRD patterns). The Cu kα ray was used for the measurement. A tube voltage and a tube current were set to 50 kV and 200 mA, respectively.

S-5000 manufactured by Hitachi, Ltd. was used to obtain images taken by a field emission scanning electron microscope (FE-SEM). Samples were dried at 70° C. and coated with gold, and then sample images were collected.

ImageJ was used as image analysis software to calculate the fiber diameter.

The water contact angle (WCA) was measured by a CA-D type water contact angle meter manufactured by Kyowa Interface Science Co., Ltd.

Tensilon universal testing machine RTC-1250A manufactured by A&D (https://www.aandd.co.jp/) was used to measure physical properties of the nonwoven fabric, etc. A crosshead speed was set to 1 mm/min. The measurement was performed according to an ASTM D638 plastic tensile test, and the samples were formed in a dumbbell shape. The temperature was a room temperature. A gauge length of the sample was set at 100 mm, and the test was performed after immersing in 10 times of phosphate-buffered saline for 15 minutes.

The appearance of the cells was observed using an Inverted microscope manufactured by Olympus corporation.

2. Method for Manufacturing an Artificial Cornea According to Examples

Next, a method for manufacturing an artificial cornea according to examples will be described.

The method for manufacturing an artificial cornea according to examples is basically the same as the method for manufacturing the artificial cornea according to the embodiment, and includes a nonwoven fabric preparation step and a gel arrangement step.

(1) Nonwoven Fabric Preparation Step (1-1) Electrospinning Step

First, polyvinyl alcohol (hereinafter referred to as "PVA") having a degree of hydrolysis of 87% to 89% was added to deionized water, and agitated at 80° C. for 4 hours to prepare a 11 wt % PVA aqueous solution. Independently, hydroxyethyl cellulose (hereinafter referred to as "HEC") was added to deionized water, and agitated at 50° C. for 6 hours to prepare a 5% (v/v) HEC aqueous solution.

Thereafter, graphite (hereinafter referred to as "GR") was added to the HEC solution such that a volume ratio is GR:HEC aqueous solution=0.1:10, and the mixture was agitated for 2 hours to prepare an HEC/GR aqueous solution. Next, HEC/GR aqueous solution was mixed with a PVA aqueous solution such that the volume ratio is HEC/GR aqueous solution:PVA aqueous solution=1:9, and agitated at room temperature for 1 hour to prepare a spinning solution. The prepared spinning solution was subject to an ultrasonic treatment to remove bubbles.

Next, an electrospinning apparatus including a power supply device, a 20 mL plastic syringe fitted with a capillary chip, a copper for connecting a positive electrode of the power supply device to the capillary chip, and a metal collector connected to a negative electrode of the power supply device was prepared, and the electrospinning was performed. A distance between the chip and the collector was 15 cm, and an applied voltage was 12 kV. During the electrospinning, a flow rate of the spinning solution was set to 1 mL/h.

In addition, the electrospinning apparatus and the components constituting the electrospinning apparatus as described above are generally known, and detailed description thereof will be omitted.

Next, the nonwoven fabric obtained by the electrospinning was cut into a size of about 4 $cm^2$, and placed in a Schale (Petri dish) having a diameter of 90 mm. 2 g of glutaraldehyde (GA), 2 g of ethanol, and 0.1 g of hydrochloric acid were prepared in a 50 mL round-bottom flask, and acetone was added thereto to prepare a 50 mL insolubilization solution. The nonwoven fabric was immersed in the insolubilization solution at room temperature for 6 hours. Thereafter, the nonwoven fabric was washed with the deionized water at 37° C. by a shaker incubator for 2 days. The deionized water was replaced with a new one every 12 hours during the washing.

Thereafter, the nonwoven fabric was cut into a circular shape having a diameter of 8 mm, and then the nonwoven fabric was dried at 37° C. for 48 hours.

(1-2) Hydroxyapatite Attachment Step

Next, the nonwoven fabric was placed in 25 mL of a 0.05 M calcium chloride ($CaCl_2$) aqueous solution set in the shaker incubator, and then kept at 37° C. for 12 hours. After 12 hours, the calcium chloride aqueous solution was replaced with 25 mL of a 0.03 M disodium phosphate ($Na_2HPO_4$) aqueous solution, and the pH was adjusted to 11 with 2 M sodium hydroxide (NaOH) aqueous solution. In this state, the nonwoven fabric was kept at 37° C. for 12 hours.

In the examples, the nonwoven fabric was prepared by performing one to three repetitions of the above cycle in order to observe influence of an attachment amount of nanoscale hydroxyapatite (hereinafter referred to as "nHA"). In addition, a nonwoven fabric not subjected to the hydroxyapatite attachment step was prepared. Thereafter, the nonwoven fabric was washed with the deionized water for 15 minutes, and dried at 37° C. Before the gel arrangement step, a through-hole having a diameter of 3 mm was formed at a center of the nonwoven fabric.

(2) Gel Arrangement Step 15 g of PVA (completely hydrolyzed) was added to 75 g of an aqueous solution of 80% dimethyl sulfoxide (DMSO), and agitated at 80° C. for 4 hours to prepare a 15 wt % PVA solution, which is a source of the aqueous polymer gel.

Next, the nonwoven fabric was immersed in the 15 wt % PVA solution, and the aqueous polymer gel was arranged by the freeze-thawing scheme. In the freeze-thawing scheme, a step of keeping the 15 wt % PVA solution and the nonwoven fabric in an environment of −20° C. for 12 hours and a step of keeping the 15 wt % PVA solution and the nonwoven fabric in an environment of room temperature for 12 hours were repeated five times.

Then, the nonwoven fabric on which the aqueous polymer gel was placed was put in water inside the shaker incubator, and washed with water at 37° C. for 2 days while replenishing the water every 12 hours to remove dimethyl sulfoxide (DMSO).

Thus, the artificial corneas according to the examples were prepared.

3. Physical Properties of an Artificial Cornea According to Examples

Hereinafter, physical properties or the like of the artificial cornea according to the examples will be observed and described with measurement results.

In the following description, an artificial cornea prepared by using a nonwoven fabric to which the nHA is not attached is denoted as an artificial cornea S0, an artificial cornea prepared by using a nonwoven fabric subject to one cycle of attaching the nHA is denoted as an artificial cornea S1, an artificial cornea prepared by using a nonwoven fabric subject to two cycles of attaching the nHA is denoted as an artificial cornea S2, and an artificial cornea prepared by using a nonwoven fabric subject to three cycles of attaching the nHA is denoted as an artificial cornea S3. In addition, the same reference numerals S0 to S3 will be used in the drawings.

Figure 3:
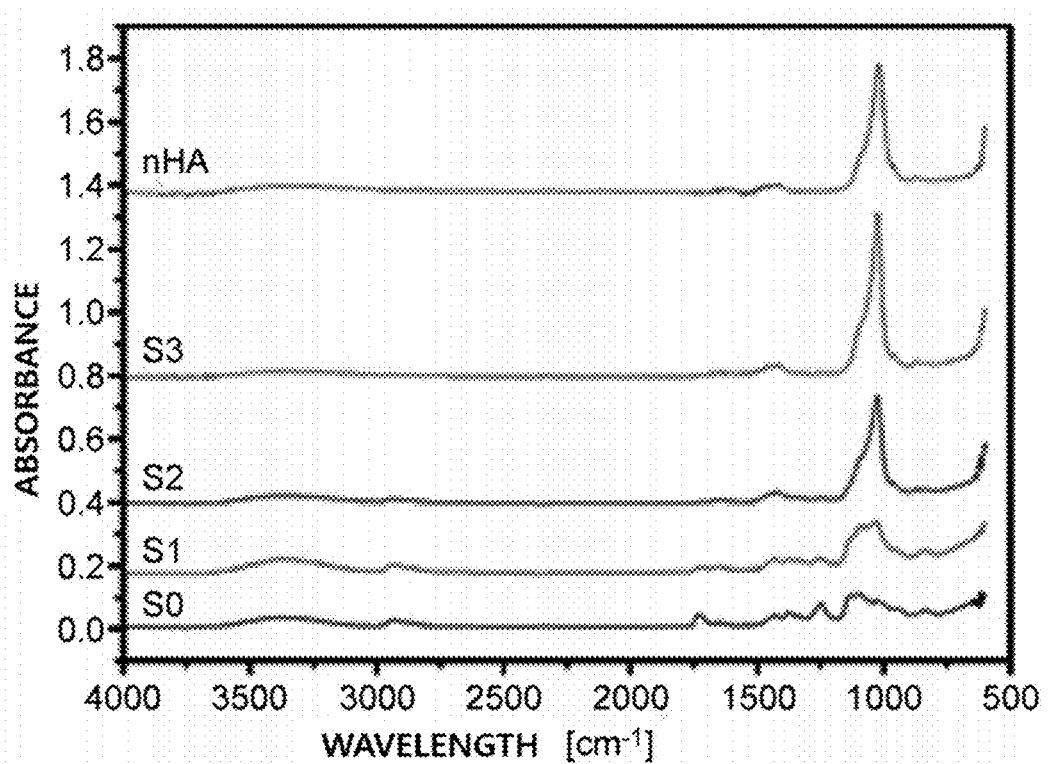
FIG. 3 is a graph showing attenuated total reflection-Fourier transform infrared spectra (ATR-FTIR spectra) of nanoscale hydroxyapatite (nHA) and nonwoven fabrics of artificial corneas according to examples.

FIG. 3 is a graph showing ATR-FTIR spectra of the nHA and the nonwoven fabrics of the artificial corneas S0 to S3 according to examples.

In the graph of FIG. 3, a horizontal axis represents a wavelength (unit: $cm^{-1}$), and a vertical axis represents absorbance. In addition, each spectrum is vertically shown to facilitate comparison, so that the absorbance on the vertical axis does not indicate absolute absorbance of each spectrum.

Figure 4:
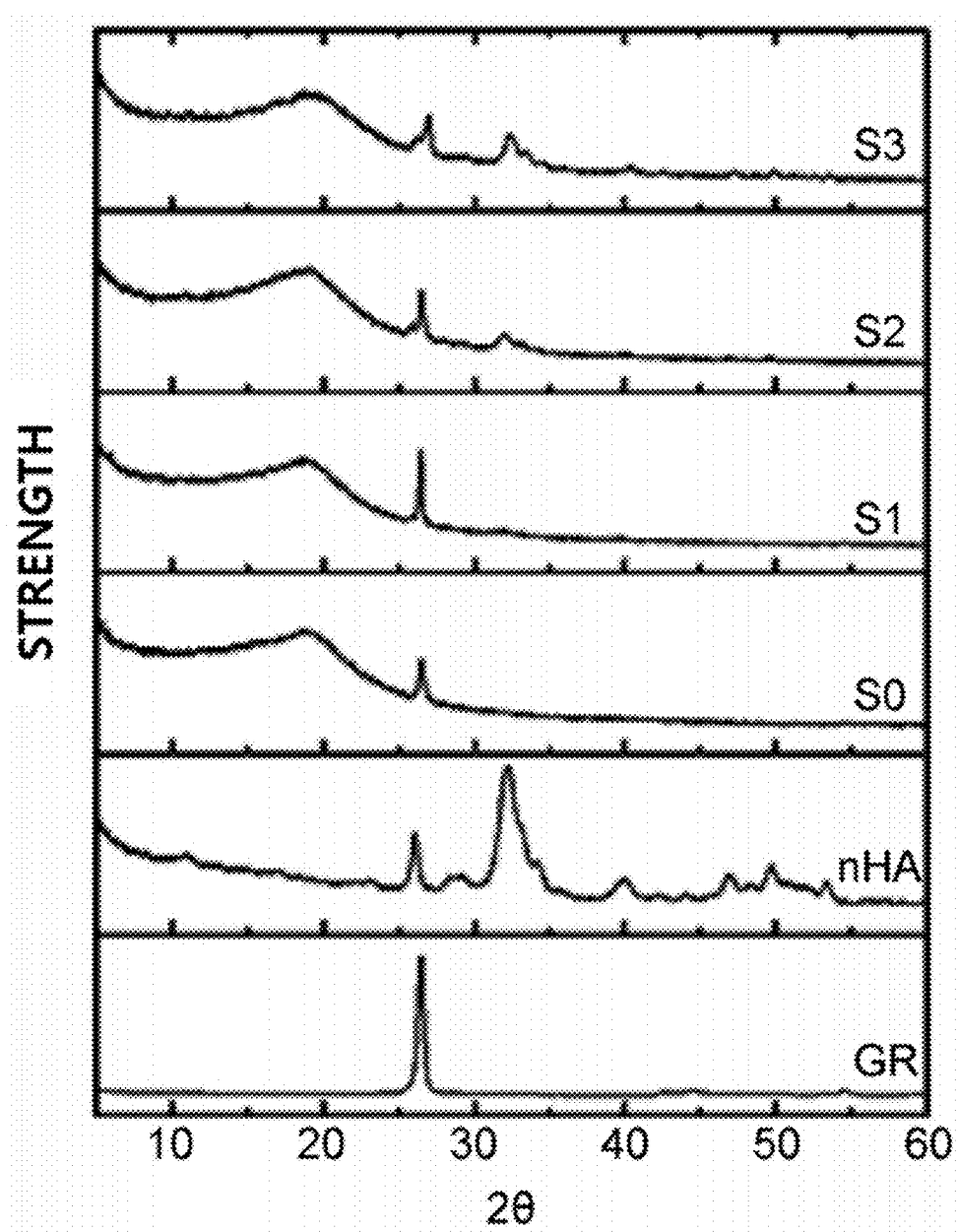
FIG. 4 is a graph showing X-ray diffraction (XRD) patterns of graphite (GR), nHA, and the nonwoven fabrics of the artificial corneas according to the examples.

FIG. 4 is a graph showing XRD patterns of GR, nHA, and the nonwoven fabrics of the artificial corneas S0 to S3 according to the examples. In the graph of FIG. 4, a horizontal axis represents 2θ, and a vertical axis represents strength (predetermined unit).

Figure 5:
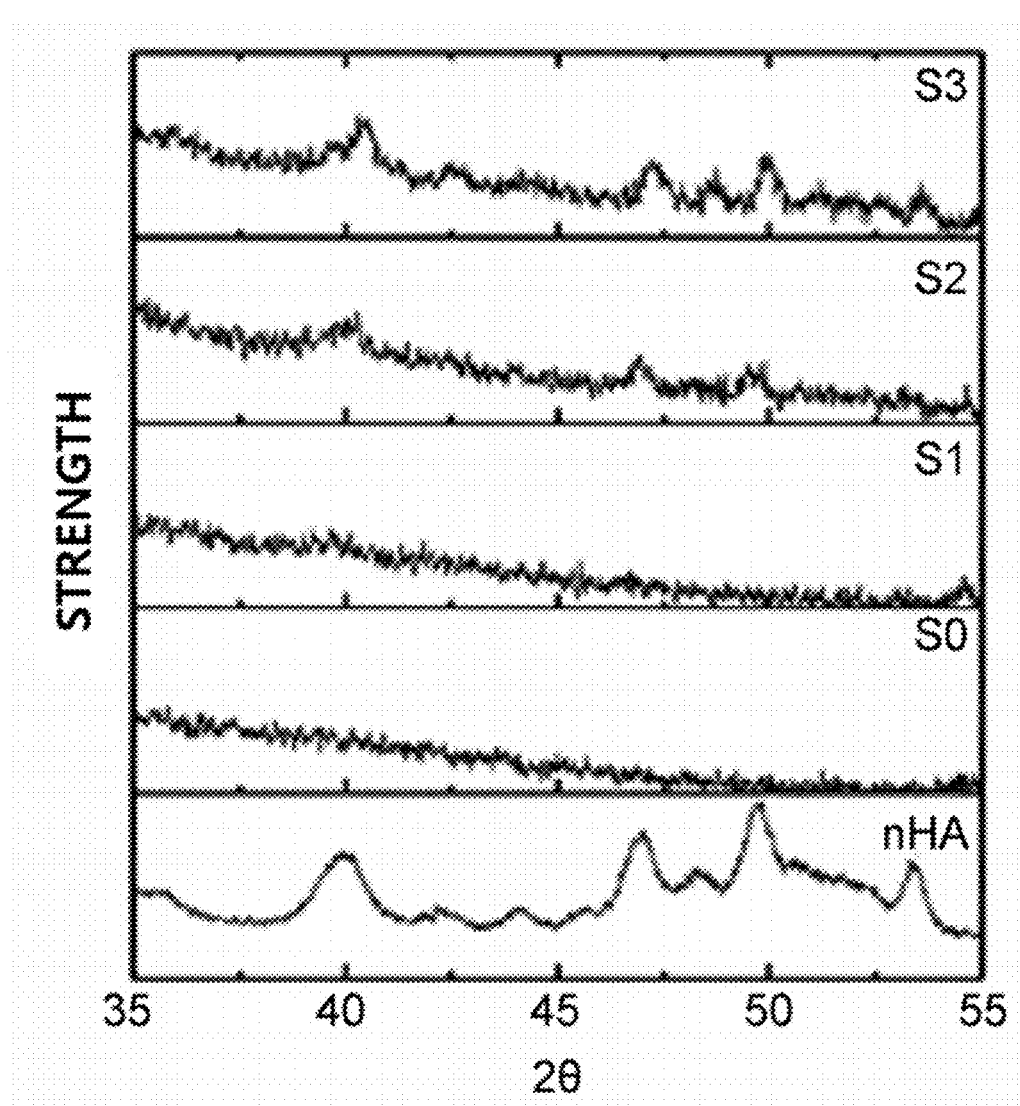
FIG. 5 is a graph showing high-resolution XRD patterns of nHA and the nonwoven fabrics of the artificial corneas according to the examples.

FIG. 5 is a graph showing high-resolution XRD patterns of nHA and the nonwoven fabrics of the artificial corneas S0 to S3 according to the examples. In the graph of FIG. 5, a horizontal axis represents 2θ, and a vertical axis represents strength (predetermined unit).

Figure 6:
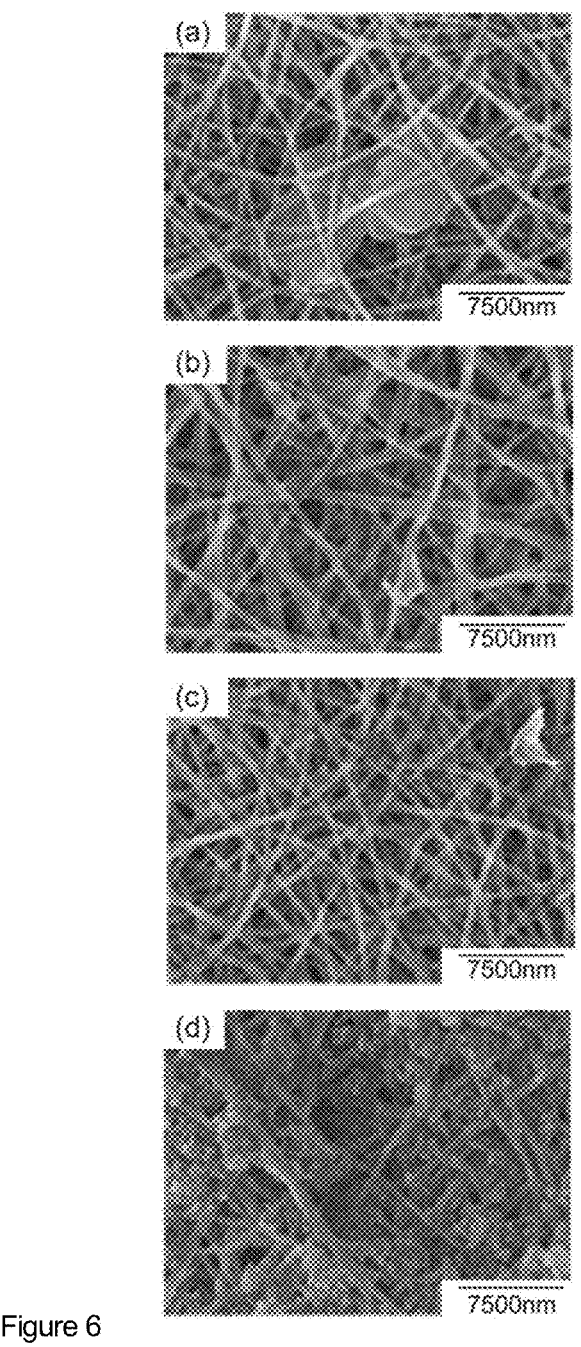
FIG. 6 is a photograph taken by a field emission scanning electron microscope (FE-SEM) showing the nonwoven fabrics of the artificial corneas according to the examples.

FIG. 6 is a photograph taken by the FE-SEM showing the nonwoven fabrics of the artificial corneas S0 to S3 according to the examples.

FIG. 6A is a photograph taken by the FE-SEM showing the nonwoven fabric of the artificial cornea S0, FIG. 6B is a photograph taken by the FE-SEM showing the nonwoven fabric of the artificial cornea S1, FIG. 6C is a photograph taken by the FE-SEM showing the nonwoven fabric of the artificial cornea S2, and FIG. 6D is a photograph taken by the FE-SEM showing the nonwoven fabric of the artificial cornea S3.

Figure 7:
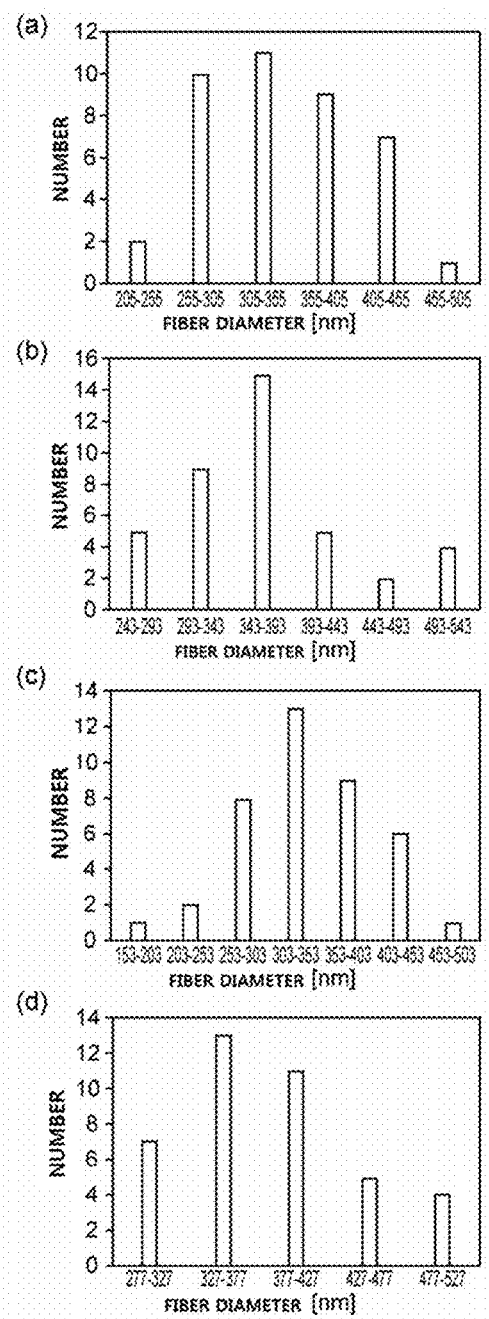
FIG. 7 is a graph showing diameter distribution of fibers constituting the nonwoven fabrics of the artificial corneas according to the examples.

FIG. 7 is a graph showing fiber diameter distribution of fibers constituting the nonwoven fabrics of the artificial corneas S0 to S3 according to the examples. FIG. 7A is a graph showing the fiber diameter distribution of the nonwoven fabric of the artificial cornea S0, FIG. 7B is a graph showing the fiber diameter distribution of the nonwoven fabric of the artificial cornea S1, FIG. 7C is a graph showing the fiber diameter distribution of the nonwoven fabric of the artificial cornea S2, and FIG. 7D is a graph showing the fiber diameter distribution of the nonwoven fabric of the artificial cornea S3. A vertical axis of the graph shown in FIG. 7 represents the number (unit: number).

Figure 8:
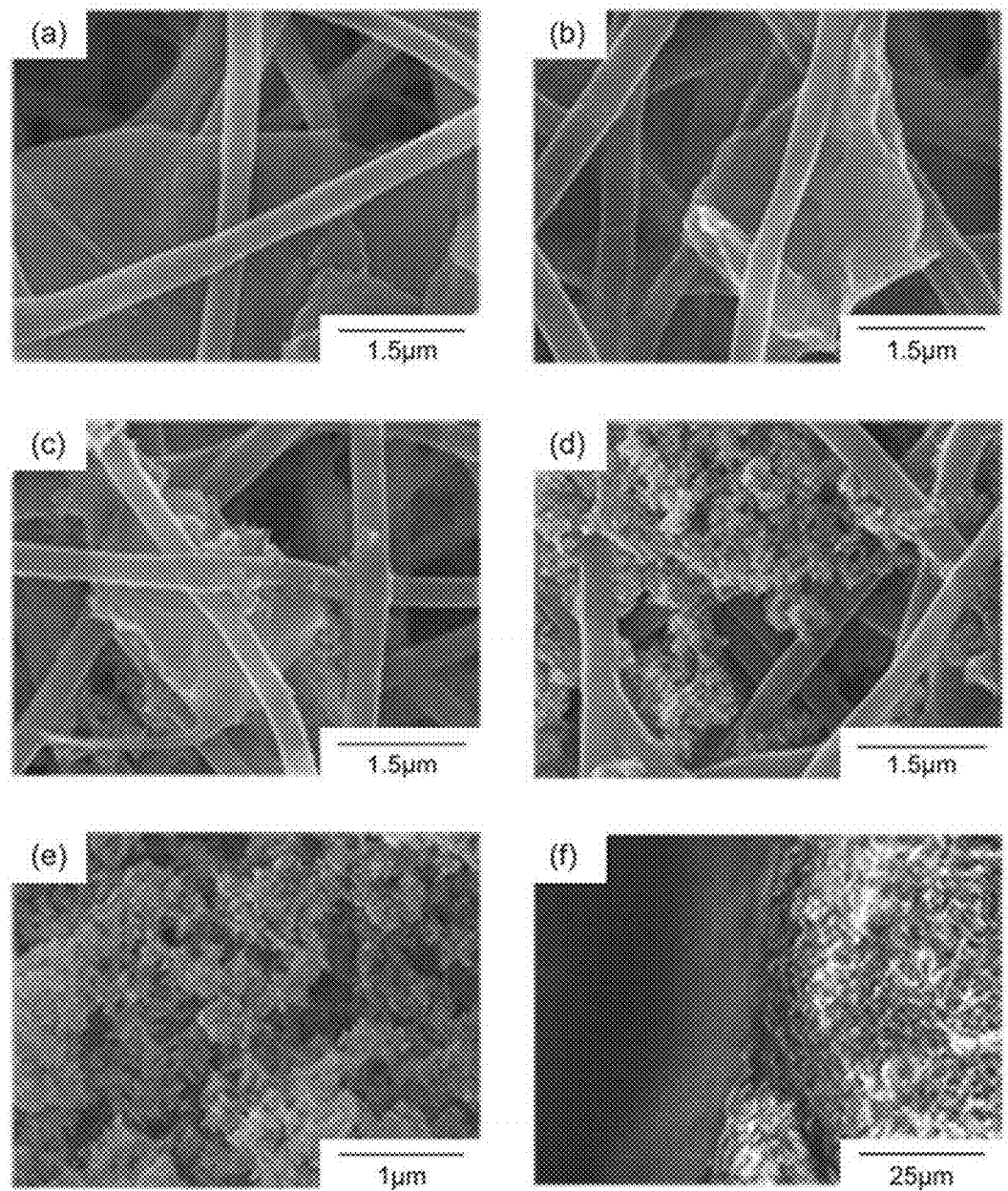
FIG. 8 is a high-resolution image taken by the FE-SEM showing nHA and the artificial corneas according to the examples.

FIG. 8 is a high-resolution image taken by the FE-SEM showing nHA and the artificial corneas S0 to S3 according to the examples. FIG. 8A is a photograph taken by the FE-SEM showing the nonwoven fabric of the artificial cornea S0, FIG. 8B is a photograph taken by the FE-SEM showing the nonwoven fabric of the artificial cornea S1, FIG. 8C is a photograph taken by the FE-SEM showing the nonwoven fabric of the artificial cornea S2, FIG. 8D is a photograph taken by the FE-SEM showing the nonwoven fabric of the artificial cornea S3, FIG. 8E is a photograph taken by the FE-SEM showing the nHA, and FIG. 8F is a photograph taken by the FE-SEM showing the nonwoven fabric of the artificial cornea S0.

Figure 9:
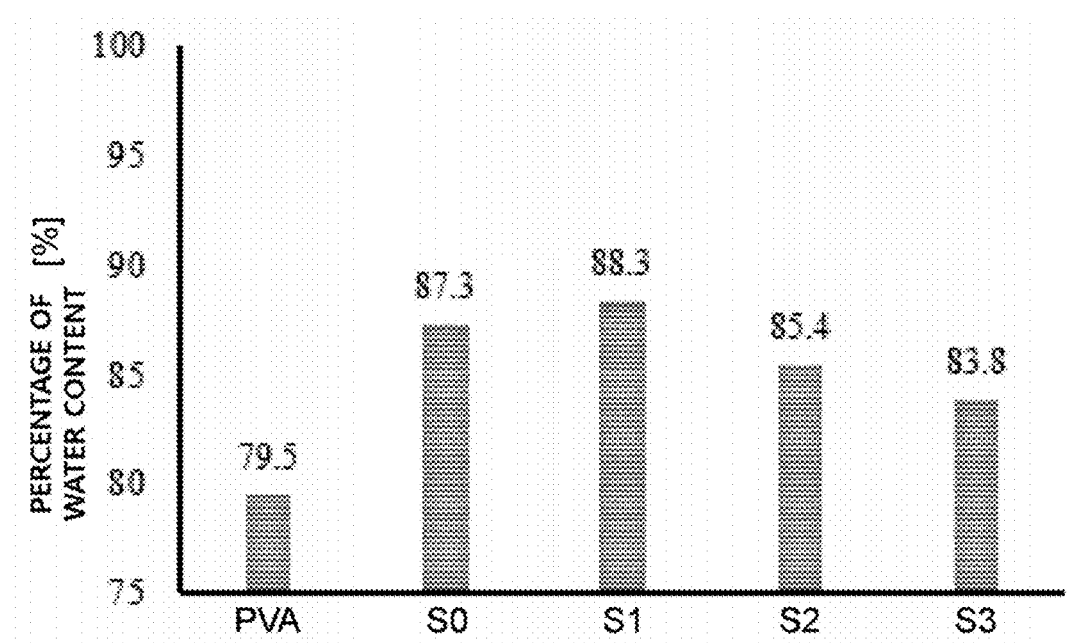
FIG. 9 is a histogram showing moisture content of polyvinyl alcohol (PVA) hydrogel and the nonwoven fabrics of the artificial corneas according to the examples.

FIG. 9 is a histogram showing moisture content of PVA hydrogel and the nonwoven fabrics of the artificial corneas S0 to S3 according to the examples. A vertical axis of the histogram shown in FIG. 9 represents the percentage of water content (unit: %).

Figure 10:
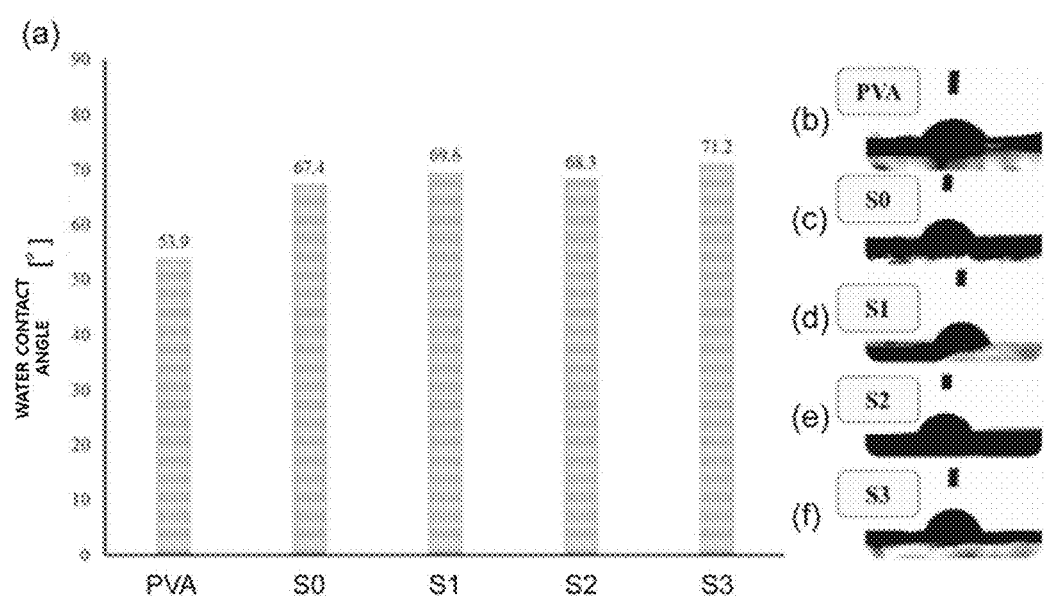
FIG. 10 is a view showing results of experiments on a water contact angle of the PVA hydrogel and the nonwoven fabrics of the artificial corneas according to the examples.

FIG. 10 is a view showing results of experiments on the water contact angle of the PVA hydrogel and the nonwoven fabrics of the artificial corneas S0 to S3 according to the examples. FIG. 10A is a histogram showing numerical values of the water contact angle, and FIGS. 10B to 10F are photographs of each sample at the time of measurement.

Figure 11:
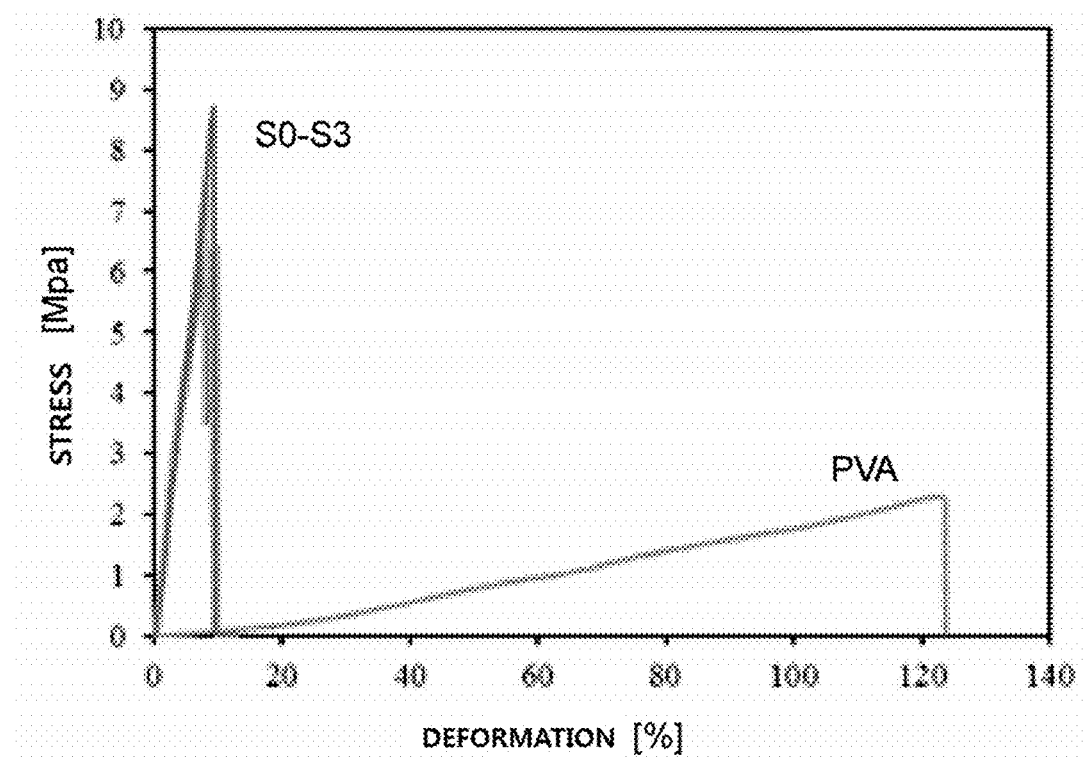
FIG. 11 is a graph showing deformation-stress curves of the PVA hydrogel and the nonwoven fabrics of the artificial corneas according to the examples.

FIG. 11 is a graph showing deformation-stress curves of the PVA hydrogel and the nonwoven fabrics of the artificial corneas S0 to S3 according to the examples. In the graph of FIG. 11, a horizontal axis represents the deformation (unit: %), and a vertical axis represents the stress (unit: MPa). In the graph of FIG. 11, since the measurement results for the nonwoven fabrics of the artificial corneas S0 to S3 tend to be almost the same, it is difficult to separate the measurement results, so that the graphs of the nonwoven fabrics of the artificial corneas S0 to S3 are summarized and shown as 'S0-S3'.

First, the ATR-FTIR spectra of nHA and the nonwoven fabrics of the artificial corneas S0 to S3 according to the examples were measured (see FIG. 3).

In the nonwoven fabrics of the artificial corneas S0 to S3, basic peaks such as a band of 3382 $cm^{-1}$ and 2931 $cm^{-1}$ associated with OH or $CH_2$, peaks at 1726 $cm^{-1}$ and 1427 $cm^{-1}$ associated with COOH or C=C bonds, and peaks at 1242 $cm^{-1}$ and 1116 $cm^{-1}$ associated with C-0 bonds were observed.

In addition, regarding nHA, basic peaks such as a band of 3382 $cm^{-1}$ due to OH symmetrical stretching, a peak at 1427 $cm^{-1}$ associated with carbonate hydroxyapatite, a band of 1020 $cm^{-1}$ due to bending vibration and stretching vibration of P—O bonds, a band of 1020 $cm^{-1}$ due to symmetrical stretching of the P—O bonds, a peak of 962 $cm^{-1}$ due to symmetrical stretching of phosphate ion ($PO4^{3-}$), and a band of 873 $cm^{-1}$ due to asymmetric stretching of the phosphate ion ($PO4^{3-}$) were observed.

In addition, as the number of cycles of attaching the nHA increases, the peak of 1020 $cm^{-1}$ due to the symmetrical stretching of the PO bonds tended to increase due to the increase of nHA, and the band of 3382 $cm^{-1}$ associated with OH tended to decrease due to the influence of calcium ions.

In other words, it was confirmed whether the nHA is successfully attached, or it was confirmed that the attachment amount of nHA can be controlled according to the number of cycles of attaching the nHA.

Next, the XRD patterns of the GR, the nHA, and the nonwoven fabrics of the artificial corneas S0 to S3 were measured (see FIG. 4). In addition, high-resolution XRD patterns were measured within a range of 35° to 55° for the nHA and the nonwoven fabrics of the artificial corneas S0 to S3 (see FIG. 5).

As a result, comparing distinguishing peak shapes of the GR and nHA with peak shapes of the artificial corneas S0 to S3 (particularly, intensities of peaks at 47°, 49.7°, and 53.4°, which are distinguishing peaks associated with nHA; see FIG. 5), it was confirmed that the attachment amount of nHA can be controlled according to the number of cycles of attaching the nHA.

Next, photographs of the nonwoven fabrics of the artificial corneas S0 to S3 were taken by the FE-SEM for observation (see FIGS. 6 and 7).

Generally, it was confirmed that soft nanofibers can be manufactured. In addition, it was confirmed that the fiber diameter of the nanofibers is 153 nm to 543 nm, which are independent from the number of cycles of attaching the nHA. 70% of the nanofibers had a fiber diameter in a range of 300 nm to 400 nm, and an average fiber diameter was generally 359 nm. In the FE-SEM image, aggregation of GR could not be observed. Particularly, in the artificial cornea S3, it was confirmed that the nHA (aggregation of a needle-shaped substance) is increased as compared with other samples.

Next, the high-resolution FE-SEM photographs of the artificial corneas S0 to S3 and the nHA were taken for observation (see FIG. 8). As a result, it was observed that the nHA having a needle-shaped structure started to aggregate in the artificial cornea S1 (see FIG. 8B), and the nHA further increased in the artificial cornea S2 and the artificial cornea S3 (see FIGS. 8C and 8D). In addition, in the high-resolution FE-SEM image of the nHA, it was confirmed that needle-shaped nHA are aggregated to form an aggregate having an average diameter of 52 nm, and this was also confirmed in the case of the artificial corneas S1 to S3.

In addition, no gap or the like was observed in the vicinity of the through-hole of the artificial cornea, and it was confirmed that the nonwoven fabric of the artificial cornea and the aqueous polymer gel (PVA hydrogel) are fixed to each other (see FIG. 8F). In addition, although FIG. 8F shows an FE-SEM image of the artificial cornea S0, similar results were obtained in other artificial corneas S1 to S3. It is determined that nonwoven fabric-vicinity-aqueous polymer gel are smoothly and continuously arranged because the aqueous polymer gel penetrates into the nonwoven fabric by several micrometers to several tens of micrometers (about 20 μm in the example) in the vicinity of the through-hole of the artificial cornea.

Next, the moisture content of the PVA hydrogel and the nonwoven fabrics of the artificial corneas S0 to S3 according to the examples were measured (see FIG. 9). The percentage of water content was calculated by measuring a weight of the sample in a state in which water is sufficiently absorbed and a weight of the sample in a properly dried state. It was confirmed that the percentage of water content of the PVA hydrogel is 79.5%, which is close to a water content value (about 78%) of a biological cornea of a human. In addition, it was confirmed that the moisture content of the nonwoven fabrics of the artificial corneas S0 to S3 are in a range of 83.8% to 88.3%. In the nonwoven fabrics, an amount of absorbing water was slightly reduced when the amount of nHA was increased, so an absorption rate tended to decrease.

Next, the water contact angles of the PVA hydrogel and the nonwoven fabrics of the artificial corneas S0 to S3 according to the examples were measured (see FIG. 10). As a result, it was confirmed that the artificial corneas S0 to S3 have greater water contact angles than the PVA hydrogel.

Next, the deformation-stress curves of the PVA hydrogel and the nonwoven fabrics of the artificial corneas S0 to S3 according to the examples were measured to examine the physical properties (see FIG. 11). As a result, as expected, it was confirmed that the nonwoven fabrics of the artificial corneas S0 to S3 have lower elasticity and higher tensile strength as compared with the PVA hydrogel. In particular, the tensile strength of the PVA hydrogel was 2.29 MPa. Meanwhile, the tensile strength of the artificial cornea S0 was 6.32 MPa, the tensile strength of the artificial cornea S1 was 7.48 MPa, the tensile strength of the artificial cornea S2 was 7.27 MPa, and the tensile strength of the artificial cornea S3 was 8.69 MPa. In addition, regarding the above results, it is determined that the tensile strength of the nonwoven fabric tends to increase as the amount of nHA increases.

4. Cytotoxicity Test on Corneal Cells

Figure 12:
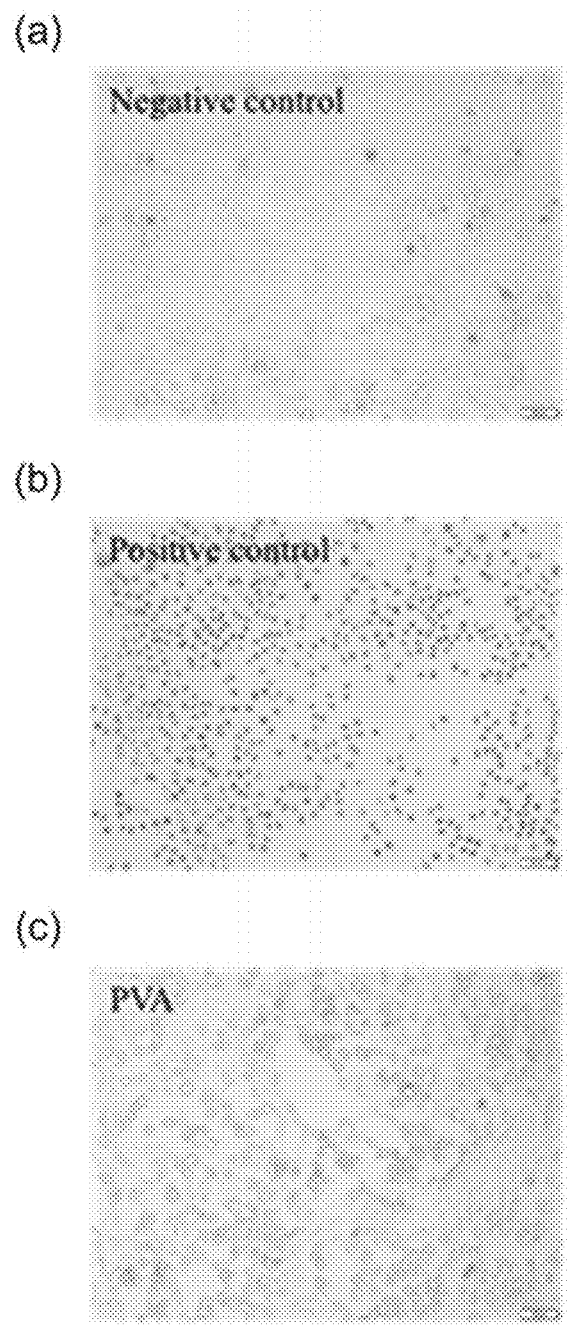
FIG. 12 is a photomicrograph showing results of a cytotoxicity test according to the examples.
Figure 13:
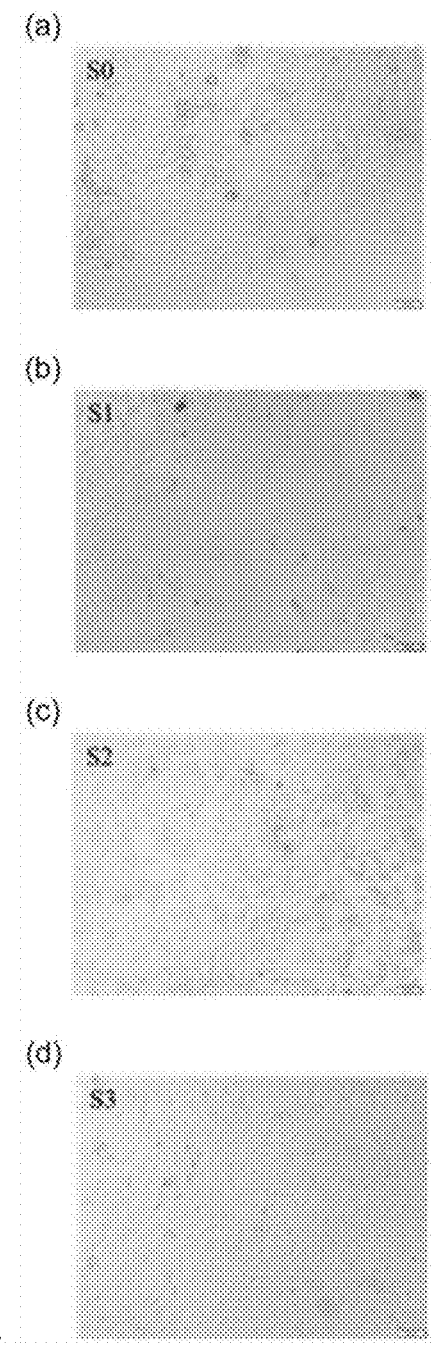
FIG. 13 is a photomicrograph showing result of the cytotoxicity test according to the examples.

FIGS. 12 and 13 are photomicrographs showing the results of the cytotoxicity test in the examples. FIG. 12A is a photograph showing a result for negative control, FIG.

12B is a photograph showing a result for positive control, and FIG. 12C is a photograph showing a results for the PVA hydrogel.

FIG. 13A is a photograph showing a result of the nonwoven fabric of the artificial cornea S0, FIG. 13B is a photograph showing a result of the nonwoven fabric of the artificial cornea S1, FIG. 13C is a photograph showing a result of the nonwoven fabric of the artificial cornea S2, and FIG. 13D is a photograph showing a result of the nonwoven fabric of the artificial cornea S3.

Next, the cytotoxicity test on human corneal epithelium (HCE) cells was performed on the PVA hydrogel and the nonwoven fabrics of the artificial corneas S0 to S3 according to the examples.

As a culture medium for culturing the human corneal epithelium cells, the Dulbecco's Modified Eagle's Medium/Ham's F-12 medium containing 10% of the newborn calf serum (NBCS), 1.05 mM of calcium chloride ($CaCl_2$), 0.5% of dimethyl sulfoxide (DMSO), 2 mg/mL of the epidermal growth factor (EFG; human body recombinant), and 1% of the insulin-transferrin-selenium (ITS) mixed reagent was used. The HCE cells were cultured using the 24-well cell culture plate until 80% confluent is achieved.

Then, the samples were directly placed in a cell layer and cultured in a fresh medium for 24 hours. After the cultivation, dead cells were stained in trypan blue and observed by a microscope. Cytotoxicity was tested under ISO10993 guidelines.

In addition, Silastic medical grade tubing (silicone elastomer tube, manufactured by Dow Corning) was used as the sample for the negative control. Further, latex gloves for aseptic surgery (manufactured by Ansell Medical, Australia) were used as the sample for the positive control.

As a result, the cells were annihilated in the positive control, whereas a small number of cell deaths occurred in the negative control. It is determined that the death of the cells is also due to physical damage occurred when the sample was placed. Regarding the PVA hydrogel and the nonwoven fabrics of artificial corneas S0 to S3 according to the examples, a ratio of the cell death was close to the negative control. In other words, it was confirmed that there is no cytotoxicity against human corneal epithelium cells.

5. Conclusion

According to the above test examples, it was confirmed that the artificial cornea can be manufactured according to the method for manufacturing the artificial corneal of the present invention.

Although the present invention has been described with reference to the above embodiments and examples, the present invention is not limited to the above embodiments and examples. The present invention can be carried out in various forms without departing from the spirit of the invention.

For example, the configurations, etc. described in the above-described embodiments and experimental examples are illustrative or specific examples, and can be changed within a range that does not degrade the effects of the present invention.

What is claimed is:

1. A method for manufacturing an artificial cornea, the method comprising:
a nonwoven fabric preparation step of preparing a nonwoven fabric formed therein with a through-hole; and
a gel arrangement step of arranging an aqueous polymer gel to cover the through-hole;
wherein the nonwoven fabric includes a composite nanofiber of polyvinyl alcohol, hydroxyethyl cellulose, and graphite (PVA-HEC-GR).

2. The method of claim 1, wherein the nonwoven fabric is formed through an electrospinning scheme using a spinning solution as a source material obtained by dispersing the graphite in a mixed solution of the polyvinyl alcohol and the hydroxyethyl cellulose.

3. The method of claim 1, wherein a hydroxyapatite (HA) is attached to the nonwoven fabric.

4. The method of claim 1, wherein the aqueous polymer gel includes a polyvinyl alcohol-based aqueous polymer gel.

5. The method of claim 4, wherein the gel arrangement step comprises arranging the aqueous polymer gel on the nonwoven fabric by a freeze-thawing scheme.

6. A method for manufacturing an artificial cornea, the method comprising:
a nonwoven fabric preparation step of preparing a nonwoven fabric formed therein with a through-hole; and
a gel arrangement step of arranging an aqueous polymer gel to cover the through-hole;
wherein the nonwoven fabric preparation step comprises attaching a hydroxyapatite to the nonwoven fabric by performing one time or several times of a cycle of immersing the nonwoven fabric in an aqueous solution of calcium chloride, and immersing the nonwoven fabric in an aqueous solution of disodium phosphate (DSP) ($Na_2HPO_4$) adjusted to pH 10 or more.

* * * * *